US00PP13797P39

(12) United States Plant Patent
Pieters

(10) Patent No.: US PP13,797 P3
(45) Date of Patent: May 13, 2003

(54) CHRYSANTHEMUM PLANT NAMED 'GEDI ONE CES'

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 09/873,902

(22) Filed: Jun. 4, 2001

(65) Prior Publication Data

US 2002/0184682 P1 Dec. 5, 2002

(51) Int. Cl.[7] ..... A01H 5/00
(52) U.S. Cl. ..... Plt./289

(58) Field of Search ..... Plt./289, 287, 286

(56) References Cited

U.S. PATENT DOCUMENTS

PP10,215 P 1/1998 Pieters ..... Plt./289

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant cultivar characterized by large decorative type inflorescences, consistent flowering response to short days, blooming consistently after 49 days of short day length, free branching habit, and bright yellow ray florets, which resist fading with age.

1 Drawing Sheet

LATIN NAME

*Dendranthema morifolium*

VARIETY

'GEDI ONE CES'

BACKGROUND OF THE INVENTION

Figure 1:
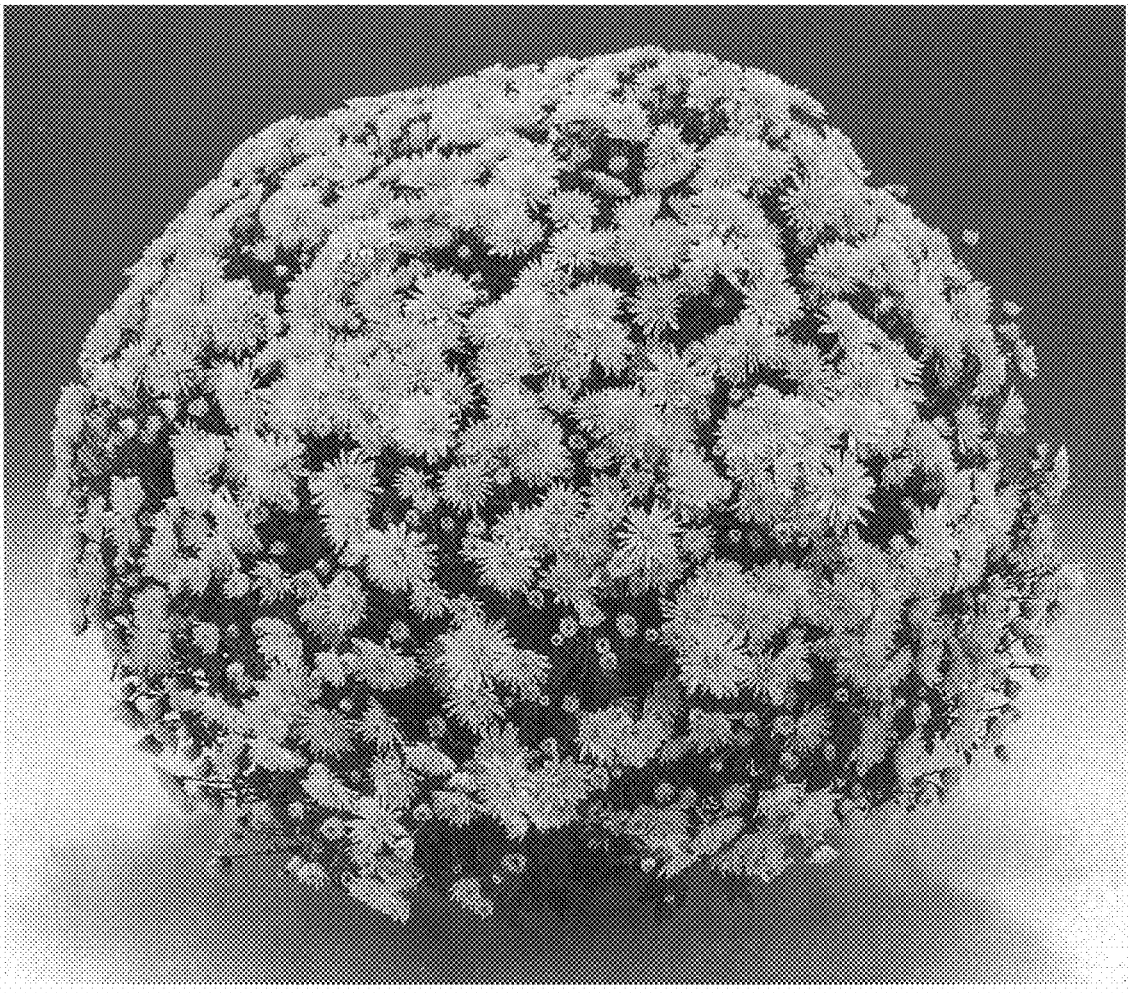

The present invention relates to a new and distinct cultivar of Chrysanthemum plant, hereinafter referred to by the cultivar name 'GEDI ONE CES.'

The new cultivar is a product of hybridization of the female parent 'Yellow Urano' (U.S. Plant Pat. No. 13,101) and the male parent 'Dark Veria' (U.S. Plant Pat. No. 10,215). The new cultivar was discovered and selected by the inventor in October 1997.

Asexual reproduction of the new cultivar by apical tip cutting and meristem tissue culture was performed in Oxnard, Calif. and has shown that the unique features of this new Chrysanthemum cultivar are stable and reproduced true to type on successive generations.

SUMMARY OF THE INVENTION

The cultivar 'GEDI ONE CES' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'GEDI ONE CES.' These characteristics in combination distinguish 'GEDI ONE CES' as a new and distinct Chrysanthemum cultivar:

1. Large decorative type inflorescence;
2. Consistent flowering response to short days, blooming consistently after 49 days of short day length;
3. Free branching habit; and 4. Bright yellow ray florets, resisting fading with age.

Plants of the new cultivar are similar to plants of the parent cultivars, 'Yellow Urano' and 'Dark Veria' in most horticultural characteristics, however plants of the new cultivar differed from plants of the parent cultivars in several characteristics. In comparison the new cultivar differed from the parent in the following characteristics:

1. The new cultivar grows taller and wider than cultivar 'Yellow Urano;'
2. The new cultivar has many more ray florets than the cultivar 'Yellow Urano;'
3. The new cultivar naturally blooms two weeks later than cultivar 'Yellow Urano;'
4. The new cultivar has individual blooms resisting fading 7 days longer than cultivar 'Yellow Urano;'
5. The new cultivar has a wider diameter flower than cultivar 'Dark Veria;'
6. The new cultivar has many more ray florets than the cultivar 'Dark Veria;'
7. The new cultivar grows taller and wider than the cultivar 'Dark Veria;' and
8. The new cultivar naturally blooms 2 weeks earlier than the cultivar 'Dark Veria.'

BRIEF DESCRIPTION OF THE PHOTOGRAPHS

The photograph shows a plant of the new cultivar which was grown in a 2-gallon container. A single cutting was grown in the container, and the plant was grown in outdoor field conditions.

DETAILED BOTANICAL DESCRIPTION

In the following description, color references are made to The Royal Horticultural Society Colour Chart except where general terms of ordinary dictionary significance are used. The following observations and measurements describe plants grown in a commercial field in Oxnard, Calif. in the month of September 2000, 115 days from rooted cuttings.

The growing conditions range from 60° to 65° F. at night to 70° to 85° F. during the day. Measurements and numerical values represent averages of typical flowering types.

Botanical classification: *Dendranthema morifolium* cultivar 'GEDI ONE CES'
Commercial classification: Garden-type Chrysanthemum
Parentage: Hybridization of female parent 'Yellow Urano' and male parent 'Dark Veria'

PROPAGATION

Time to rooting: 7 to 14 days at approximately 21° C.
Root description: Fine, fibrous

PLANT

Growth habit: Mounding herbaceous perennial
Height: Approximately 25 cm
Growth rate: Moderate
Plant spread: Approximately 29 cm
Branching characteristics: Free Branching

FOLIAGE

Leaf:
*Arrangement.*—Alternate single.
*Average length.*—Approximately 6.8 cm.
*Average width.*—Approximately 3.2 cm.
*Shape of blade.*—Ovate.
*Apex.*—Acuminate.
*Base.*—Attenuate.
*Attachment.*—Stalked.
*Margin.*—Pinnately lobed and toothed.
*Texture of top surface.*—Lightly pubescent.
*Texture of bottom surface.*—Lightly pubescent.
*Color.*—young foliage upper side: Near 138A young foliage under side: Near 138B mature foliage upper side: Near 137A mature foliage under side: Near 137A venation upper side: Near 138C venation under side: Near 138C.

Petiole:
*Average length.*—Approximately 1.5 cm.
*Color.*—138B.
*Diameter.*—3 mm.

BLOOM

Inflorescence:
*Flowering habit.*—Induced by darkness period greater than 13.5 hours, approximately 49 days of appropriate day length required to induce and develop blooms.
*Inflorescence form.*—Decorative.
*Natural flowering season.*—Approximately the last week in August and first week in September.
*Number of inflorescences per stem.*—Approximately 15.
*Inflorescence diameter.*—Approximately 6 cm.
*Inflorescence depth.*—1.7 cm.
*Inflorescence longevity on plant.*—Approximately 26–29 days.
*Persistence.*—Persistent.

Ray florets:
*Appearance.*—Matte.
*Texture.*—Smooth.
*Average number per flower.*—200.
*Shape.*—Oblanceolate.
*Margin.*—Entire.
*Apex.*—Obtuse.
*Length.*—Approximately 3.4 cm.
*Width.*—Approximately 0.8 cm.
*Color.*—upper surface at first opening: Near 16A upper surface at maturity: Near 17C upper surface at fading: Near 16A under surface at first opening: Near 15C under surface at maturity: Near 16A under surface at fading. Near 16B.

Disc florets:
*Appearance.*—Shiny.
*Texture.*—Smooth.
*Average number per flower.*—Approximately 60.
*Shape.*—Cylindric.
*Apex.*—Obtuse.
*Average length.*—Approximately 1 cm.
*Average width.*—Approximately 0.2 cm.
*Color.*—at first opening: Near 13C at maturity: Near 12B at fading: Near 15C.

Peduncle:
*Length.*—at terminal end (shortest): Approximately 4 cm at lateral end (longest): Approximately 9 cm Strength: Moderate.
*Surface texture.*—Lightly pubescent.
*Color.*—Near 137C.
*Habit.*—Erect.

Inflorescence bud:
*Length.*—Approximately 1 cm.
*Diameter.*—Approximately 1 cm.
*Form.*—Globular.
*Color.*—Near 15A.

Phyllaries:
*Appearance.*—Matte.
*Texture.*—Lightly pubescent.
*Number.*—Approximately 30 to 40.
*Shape.*—Ovate.
*Margin.*—Entire.
*Apex.*—Acute.
*Diameter.*—Approximately 0.3 cm.
*Length.*—Approximately 0.6 cm.
*Color.*—upper side. Near 137A under side: Near 137A.

REPRODUCTIVE ORGANS

Ray florets:
*Number of pistils per flower.*—1.
*Stigma shape.*—2 branched.
*Stigma color.*—Near 16D.
*Style color.*—Near 16D.
*Style length.*—0.5 cm.
*Stamens.*—Absent.

Disc florets:
*Number of pistils per flower.*—1.
*Stigma shape.*—Cylindric.
*Style length.*—0.5 cm.
*Number of stamens per flower.*—Approximately 5.
*Anther shape.*—Tubular.
*Anther color.*—Near 16A.
*Pollen color.*—Near 17C.

Seed production: Commercially, this plant is not used or observed in a stage wherein seeds would be produced. Therefore, seed production has not been observed to date.

Disease resistance: Neither resistance nor susceptibility to diseases and pests have been observed to date in this cultivar.

What is claimed is:

1. A new and distinct cultivar of Chrysanthemum plant named 'GEDI ONE CES' as herein illustrated and described.

* * * * *